United States Patent [19]

Studier

[11] Patent Number: 5,407,799
[45] Date of Patent: Apr. 18, 1995

[54] METHOD FOR HIGH-VOLUME SEQUENCING OF NUCLEIC ACIDS: RANDOM AND DIRECTED PRIMING WITH LIBRARIES OF OLIGONUCLEOTIDES

[75] Inventor: F. William Studier, Stony Brook, N.Y.

[73] Assignee: Associated Universities, Inc., Washington, D.C.

[21] Appl. No.: 135,317

[22] Filed: Oct. 12, 1993

Related U.S. Application Data

[63] Continuation of Ser. No. 779,290, Oct. 18, 1991, abandoned, which is a continuation-in-part of Ser. No. 407,238, Sep. 14, 1989, abandoned.

[51] Int. Cl.[6] .......................... C12Q 1/68; C12P 19/34
[52] U.S. Cl. ............................: 435/6; 435/91.1; 935/77
[58] Field of Search ................................. 435/6, 91.1

[56] References Cited

U.S. PATENT DOCUMENTS 5,043,272 8/1991 Hartley .............................. 435/91.1

OTHER PUBLICATIONS

Binns et al., J. Virol. Meth. 12:265–269 (1985).
Feinberg et al., Anal. Biochem. 132:6–13 (1983).
Roberts, Science 242:1244–1246 (1988).
Sanger et al., J. Mol. Biol. 143:161–178 (1988).

*Primary Examiner*—Stephanie W. Zitomer
*Attorney, Agent, or Firm*—Margaret C. Bogosian

[57] ABSTRACT

Random and directed priming methods for determining nucleotide sequences by enzymatic sequencing techniques, using libraries of primers of lengths 8, 9 or 10 bases, are disclosed. These methods permit direct sequencing of nucleic acids as large as 45,000 base pairs or larger without the necessity for subcloning. Individual primers are used repeatedly to prime sequence reactions in many different nucleic acid molecules. Libraries containing as few as 10,000 octamers, 14,200 nonamers, or 44,000 decamers would have the capacity to determine the sequence of almost any cosmid DNA.

Random priming with a fixed set of primers from a smaller library can also be used to initiate the sequencing of individual nucleic acid molecules, with the sequence being completed by directed priming with primers from the library. In contrast to random cloning techniques, a combined random and directed priming strategy is far more efficient.

18 Claims, 2 Drawing Sheets

VECTOR PRIMING (1.00)
+ RANDOM PRIMING (0.35)

COMPLEMENTARY PRIMING (1.00)

DIRECTED EXTENSION (0.80 – 0.93)

COMPLEMENTARY SEQUENCES (1.00)

VECTOR PRIMING (1.00)
+ RANDOM PRIMING (0.35)

COMPLEMENTARY PRIMING (1.00)

DIRECTED EXTENSION (0.80 – 0.93)

COMPLEMENTARY SEQUENCES (1.00)

METHOD FOR HIGH-VOLUME SEQUENCING OF NUCLEIC ACIDS: RANDOM AND DIRECTED PRIMING WITH LIBRARIES OF OLIGONUCLEOTIDES

This invention was made with Government support under contract number DE-AC02-76CH00016, between the U.S. Department of Energy and Associated Universities, Inc. The Government has certain rights in the invention.

This application is a file wrapper continuation of application Ser. No. 779,290, filed Oct. 18, 1991, now abandoned, which is a continuation-in-part of patent application Ser. No. 407,238, filed Sep. 14, 1989, now abandoned.

BACKGROUND OF THE INVENTION

The ability to determine nucleotide sequences has had enormous impact on biology, medicine and biotechnology. An appreciation of the benefits of knowing the nucleotide sequences of genes, chromosomes, and entire genomes has led to the current proposals to determine the nucleotide sequence of the human genome and the genomes of other well studied or economically important organisms.

Cloning and mapping specific DNA fragments is an important part of the strategy for sequencing large genomes. The entire human genome of about $3 \times 10^9$ base pairs could be contained in a set of about 100,000 cosmids, each of which contains about 40,000 or more base pairs of human DNA. Even larger segments can be cloned in yeast artificial chromosomes. The genome sequencing problem then reduces to the problem of sequencing a large number of DNAs of 40,000 or more base pairs. Such an enterprise represents a tremendous increase in scale over the most ambitious sequencing projects that have been undertaken heretofore. If cosmids were sequenced at the rate of one a day, a formidable task for a sequencing center using today's technology, centuries would be required to complete the task.

Currently useful methods for determining nucleotide sequence involve generating nucleic acid fragments having defined ends and resolving them according to size, using gel electrophoresis. These defined fragments are produced chemically (Maxam & Gilbert, Proc. Nat. Acad. Sci. USA, 74, 560–564 (1977); Methods in Enzymology 65, 499–560 (1980)), enzymatically (Sanger et al., Proc. Nat. Acad. Sci. USA 74, 5463–5467 (1977)), or by some combination of the two, and are typically identified in electrophoresis patterns by radioactivity, fluorescence or chemical reactivity.

The enzymatic sequencing technique has been highly developed, and several different DNA polymerases and reverse transcriptases are used for this purpose. These enzymes can be used for sequencing double-stranded or single-stranded DNA or RNA. Oligonucleotide primers direct DNA synthesis from a specific site in the molecule, which generates the common end needed for sequence analysis. The variable end is typically generated by incorporation of specific chain terminators, such as dideoxynucleotide triphosphates, or by incorporation of nucleoside triphosphate derivatives and subsequent cleavage of the molecule at the site of incorporation.

Specific priming is critical for the success of the enzymatic sequencing technique. Much is known about the specific association between oligonucleotides and longer nucleic acids, and about the ability of specifically associated oligonucleotides to prime DNA synthesis by the enzymes used for nucleotide sequencing (for example, M. Smith, in "Methods of DNA and RNA Sequencing", edited by S.M. Weissman, Praeger Publishers, New York, pp 23–68, 1983). Oligonucleotides as short as three or four bases long have been reported to prime DNA synthesis, and a mixture of hexamers is widely used to prime random DNA synthesis for labeling hybridization probes. Oligonucleotides of length 6 or longer are useful for priming specific sequencing reactions.

In practice, blocks of nucleotide sequence up to several hundred but rarely as long as a thousand nucleotides can be determined from the products of a single sequencing reaction or set of reactions. Cosmid DNAs, and in fact most nucleic acids of interest, are much longer than the few hundred nucleotides that is the basic unit of sequence determination. Therefore, a substantial part of the effort involved in sequencing genes or genomes, or almost any nucleic acid, must be devoted to obtaining and assembling the many individual blocks of a few hundred nucleotides of sequence that make up the entire nucleic acid to be sequenced. If an average of 500 nucleotides of sequence could be obtained in each analysis, a minimum of 160 sets of sequencing reactions would have to be prepared and analyzed to obtain the sequence of both strands of one cosmid DNA.

Several strategies have been developed for obtaining and ordering the many individual blocks of sequence needed to determine the entire sequence of larger molecules. One strategy is to use restriction enzymes to obtain and map specific fragments of the DNA molecule. The nucleotide sequences of appropriate fragments are determined, and the sequence of the entire molecule is assembled :from the known positions of the fragments. As example of the use of this strategy is the determination of the sequence of T7 DNA, a double-stranded molecule about 40,000 bp long (Dunn & Studier, J. Mol. Biol. 166, 477–535 (1983)). However, such a strategy is too labor intensive to be economical for sequencing large numbers of DNA molecules.

A more typical strategy is to subclone random fragments of the DNA into a cloning vector, typically derived from M13. The sequence of the cloned DNA is usually determined by the enzymatic sequencing technique, starting from a unique priming site within the vector DNA. Randomly selected subclones are sequenced, and the sequence of the original DNA is reconstructed from overlaps among the many blocks of sequence obtained from the different subclones. The sequence of lambda DNA, about 48,500 bp long (Sanger et al., J. Mol. Biol. 162, 729–773 (1982)), was determined by extensive use of such a strategy. Although relatively efficient in the early stages, a random cloning strategy becomes highly redundant in the later stages. In a purely random strategy, perhaps ten times the minimum possible number of sequence analyses may have to be done before all of the blocks of sequence can be overlapped. In practice, labor intensive mapping techniques are often used to close gaps.

Modifications have improved the efficiency of random cloning strategies. The length of continuous sequence that can be generated from a single priming site in a cloning vector can be extended considerably by generating sets of nested deletions that bring different portions of the DNA close to the priming site (Barnes, Methods in Enzymology, 152, 538–(1987)). However, this remains relatively labor intensive for a large scale sequencing effort. Multiplexing improves sequencing efficiency by allowing a single gel electrophoresis pattern to be probed repeatedly to determine the sequence of many different cloned DNAs (Church & Kieffer-Higgins, Science 240, 185–188 (1988)). However, all subcloning strategies suffer from the necessity to prepare many different clones and isolate DNA from each of them, an effort that will typically be comparable to that required to do the sequence analyses themselves.

A directed priming, or "walking" strategy allows the sequence to be determined directly from a nucleic acid molecule of interest without mapping or subcloning, a considerable savings in effort. To use directed priming, at least a small portion of the nucleotide sequence in the molecule must be known or determined in some other way. This known sequence information is used to synthesize a primer for enzymatic sequencing reactions that will extend the sequence into the unknown region. Such primers are synthesized by well known techniques or can be purchased commercially and are typically at least 16 nucleotides long, so as to be unique in the entire molecule. In order to continue extending the sequence further along the molecule, a new primer must be synthesized for every few hundred nucleotides of sequence obtained. Although a directed priming strategy eliminates the considerable effort needed for mapping or subcloning, the cost of primers nevertheless makes the directed priming strategy very expensive for large scale sequencing.

The recently described polymerase chain reaction (PCR) for amplifying specific segments of a DNA molecule is also being used to prepare samples for sequencing (Saiki et al., Science 239, 487–491 (1988); Stoflet et at., Science 239, 491–494 (1988)). This technique can eliminate the subcloning steps, and the PCR primers themselves can be used as primers for sequencing by the enzymatic technique. However, the use of this technique requires knowledge of the nucleotide sequence flanking the region to be amplified, information that is generally not available at the outset, and the cost of primers would be comparable to that for the directed priming strategy.

Although determination of nucleotide sequences has become routine, high volume sequencing is still a difficult problem. The need for methods that allow more efficient high volume sequencing is widely recognized and is being addressed in various ways. Machines are being developed to carry out sequencing reactions and to automate DNA sample preparation and collection of data. Completely novel sequencing methods that do not require resolution of DNA fragments by gel electrophoresis are also being explored. For example, Drmanac et al. (Genomics 4, 114–128 (1989)) have proposed a method based on the pattern of hybridization of oligonucleotides to the DNA to be sequenced. However, these initiatives have not yet had a practical impact.

The current state of the art in high volume sequencing was summarized in a brief report in Science (242, 1245, Dec. 2, 1988). Bart Barrell and Ellson Chen, whose laboratories have led the way in high volume sequencing and had sequenced the largest contiguous stretches of DNA at that time, reportedly concluded that the current technology realistically allows one skilled technician to sequence about 50,000 bases a year, and even that output is difficult to sustain. This rate of sequencing is still far short of the capacity needed for projects like sequencing the human genome.

SUMMARY OF THE INVENTION

The present invention is directed to a more efficient method for determining the sequence of nucleotides in nucleic acids. The method greatly reduces the cost and effort of nucleotide sequencing and is particularly suitable for very large scale sequence determinations such as the proposed determination of the nucleotide sequence of the entire human genome.

The present invention provides methods for improving the efficiency and economy of enzymatic nucleotide sequencing. The methods include a random priming method for determining the sequence of nucleotides in parts of a nucleic acid molecule where the sequence is not known, the method comprising the steps of:

(a) mixing said nucleic acid molecule with a primer or primer combination under conditions suitable for forming a primed substrate for DNA synthesis by a polymerizing enzyme that is suitable for nucleotide sequencing, said primer or primer combination having a length and composition such that the average number of priming sites in those parts of the nucleic acid molecule where the sequence of nucleotides is not known is expected statistically to be between 0.05 and 4.5, but excluding Primers and primer combinations that would prime in any parts of the nucleic acid molecule where the sequence of nucleotides is known, said mixing being either previous to or simultaneous with step (b);

(b) incubating the mixture of step (a) with a polymerizing enzyme under conditions suitable for primed synthesis of DNA that can be used for determining nucleotide sequence;

(c) analyzing the reaction products to determine the sequence of a block of nucleotides in any DNA that was synthesized from a single priming site in the nucleic acid molecule; and (d) repeating steps (a)–(c), using different primers or primer combinations, until one or more blocks of nucleotide sequence have been determined.

The present invention further provides a directed priming method that repeatedly uses the same primers for determining or confirming the sequence of nucleotides in different nucleic acid molecules for which at least a portion of the nucleotide sequence is known, the method comprising the steps of:

(a) selecting a primer having 8, 9 or 10 bases, the primer being perfectly complementary to one and only one site in the known sequence of nucleotides in a nucleic acid molecule, said site being located so that the primer, by associating at said site, is capable of priming a polymerizing enzyme to synthesize DNA complementary to a region of the nucleic acid molecule where the nucleotide sequence is to be determined or confirmed, and said primer being obtained from a primer library or being newly prepared and the unused portion being deposited in a primer library;

(b) mixing said primer and nucleic acid molecule under conditions suitable for forming a primed substrate for DNA synthesis by a polymerizing enzyme that is suitable for nucleotide sequencing, said mixing occurring under conditions where perfect pairing is sufficiently greater than mismatched pairing that nucleotide sequence can be determined if exactly one perfect pairing site exists in the nucleic acid molecule, and said mixing being either previous to or simultaneous with step (c);

(c) incubating the mixture of step (b) with a polymerizing enzyme under conditions suitable for primed synthesis of DNA that can be used for determining nucleotide sequence;

(d) analyzing the reaction products to determine the sequence of nucleotides in any DNA that was synthesized from a single priming site in the nucleic acid molecule;

(e) repeating steps (a)–(d) until the desired sequences have been determined or until all blocks of nucleotide sequence merge or reach the ends of the molecule; and (f) repeating steps (a)–(e) to determine nucleotide sequences of different nucleic acid molecules.

Additionally, the present invention provides a combined random and directed priming method that repeatedly uses the same primers for determining the sequence of nucleotides in different nucleic acid molecules, the method comprising the steps of:

(a) mixing a nucleic acid molecule with a random primer or primer combination under conditions suitable for forming a primed substrate for DNA synthesis by a polymerizing enzyme that is suitable for nucleotide sequencing, said random primer or primer combination having a length or lengths and composition such that the average number of priming sites in those parts of the nucleic acid molecule where the sequence of nucleotides is not known is expected statistically to be between 0.05 and 4.5, but excluding primers and primer combinations that would prime in any parts of the nucleic acid molecule where the sequence of nucleotides is known, said mixing being either previous to or simultaneous with step (b);

(b) incubating the mixture of step (a) with a polymerizing enzyme under conditions suitable for primed synthesis of DNA that can be used for determining nucleotide sequence;

(c) analyzing the reaction products to determine the sequence of nucleotides in DNA that was synthesized from a single priming site in the nucleic acid molecule;

(d) repeating steps (a)–(c), using different random primers or primer combinations, sequentially or in parallel, until one or more blocks of nucleotide sequence have been determined;

(e) selecting a directed primer that is perfectly complementary to one and only one site in the known sequence of nucleotides in the nucleic acid molecule, whether said sequence was previously known or determined in steps (a)–(d), said site being located so that the directed primer, by associating at said site, is capable of priming a polymerizing enzyme to synthesize DNA complementary to a region of the nucleic acid molecule where the nucleotide sequence is to be determined or confirmed, and said directed primer being obtained from a primer library or being newly prepared and the unused portion being deposited in a primer library;

(f) mixing said directed primer and nucleic acid molecule under conditions suitable for forming a primed substrate for DNA synthesis by a polymerizing enzyme that is suitable for nucleotide sequencing, said mixing occurring under conditions where perfect pairing is sufficiently greater than mismatched pairing that nucleotide sequence can be determined if exactly one perfect pairing site exists in the nucleic acid molecule, and said mixture being either previous to or simultaneously with step (g);

(g) incubating the mixture of step (f) with a Polymerizing enzyme under conditions suitable for primed synthesis of DNA that can be used for determining nucleotide sequencing;

(h) analyzing the reaction products to determine the sequence of nucleotides in any DNA that was synthesized from a single priming site in the nucleic acid molecule;

(i) repeating steps (e)–(h) until the desired sequences have been determined or until all blocks of nucleotide sequence merge or reach the ends of the molecule; and (j) repeating steps (a)–(i) to determine nucleotide sequences of different nucleic acid molecules.

DETAILED DESCRIPTION OF THE DRAWINGS

Figure 1:
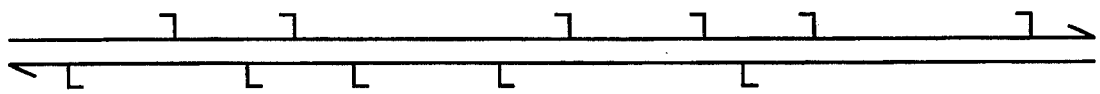
Figure 1:
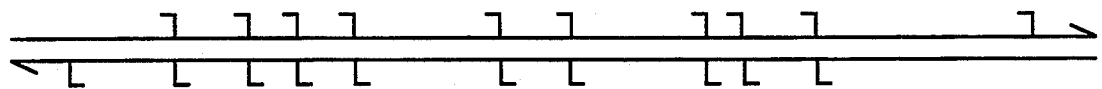
Figure 1:
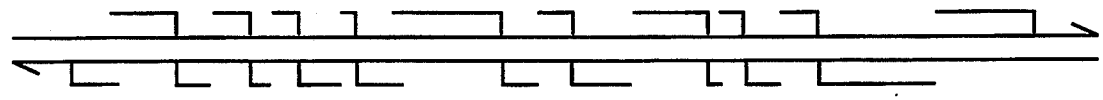
Figure 1:
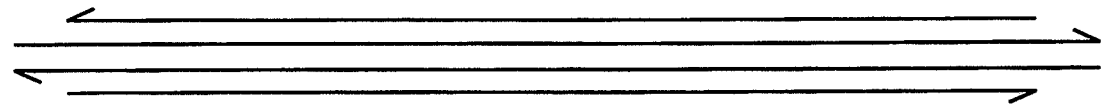

FIG. 1. Sequencing the cloned portion of a cosmid DNA by random and directed priming. Line lengths are to scale for an unknown sequence of 40,000 bp, vector sequences of 2,500 bp at each end, and primings that produce 500 nucleotides of sequence each. The expected fraction of unique primings at each stage is given; during directed extension this fraction would be 0.40–0.74 for octamer primers, 0.80–0.93 for nonamers (as shown), or 0.94–0.98 for decamers (Table 2). Priming from within the vector sequences into the ends of the cloned DNA is assumed to use primers that are long enough to be unique.

Figure 2:
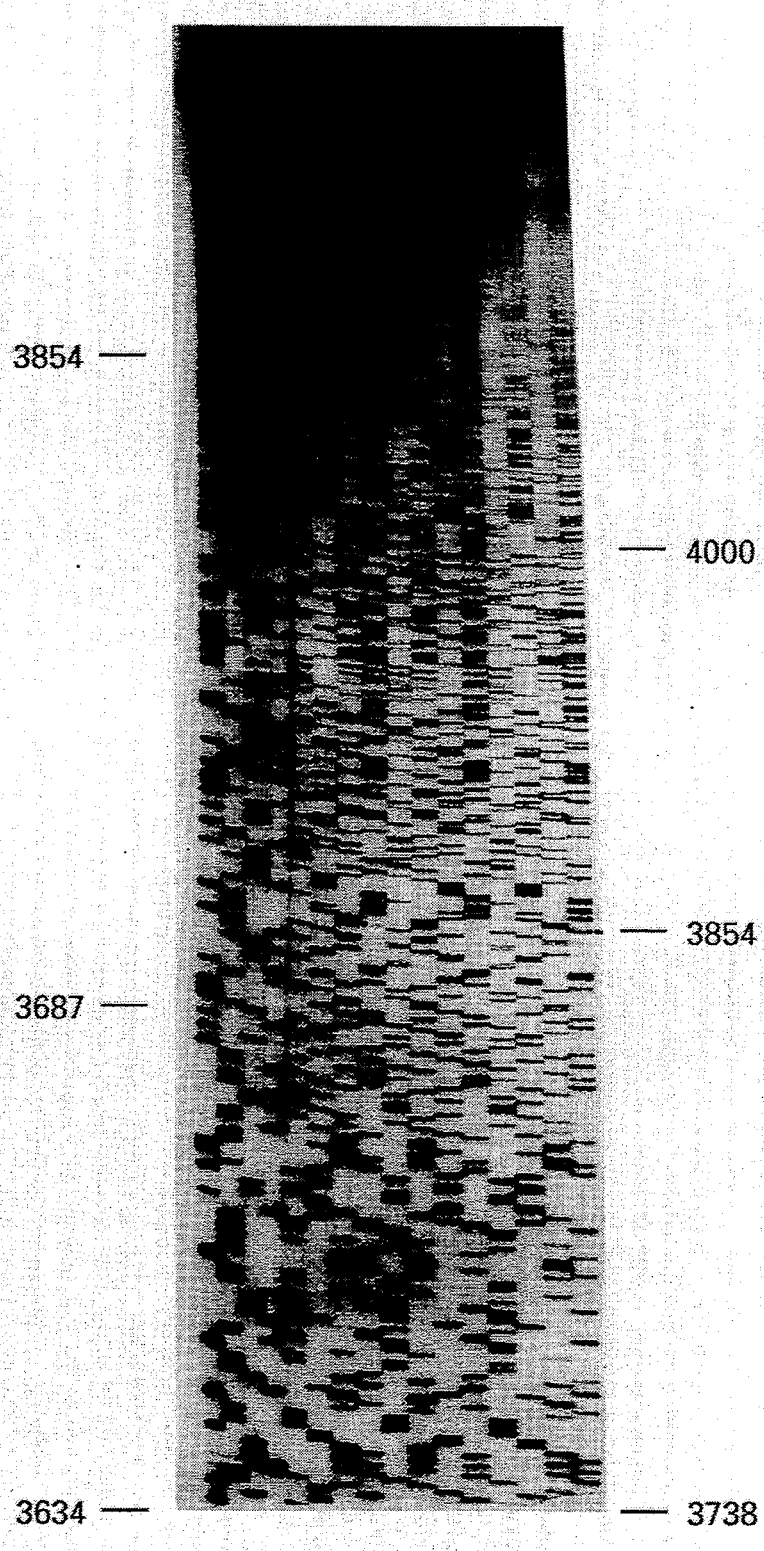

FIG. 2. Autoradiogram showing nucleotide sequence primed by an octamer primer in T7 DNA, as described in Example 1.

DETAILED DESCRIPTION OF THE INVENTION

The invention teaches random and directed priming methods wherein a statistical approach greatly improves the efficiency and economy of enzymatic nucleotide sequencing. Individual preparations of oligonucleotide primers typically provide enough material for hundreds of thousands of primings and the invention teaches methods for efficient use of this material to obtain sequence information from many different nucleic acid molecules. The methods do not require mapping or subcloning and are applicable to nucleic acid molecules of any size suitable for primed enzymatic sequencing.

The invention relates to the use of primers, selected from a primer library, to determine or confirm the sequence of nucleotides in nucleic acid molecules for which at least a portion of the nucleotide sequence is known. The primer library is a central supply of primers, a collection of different primers where each primer in the collection is present in sufficient quantity so that samples can be removed to be used in many sequencing reactions. The sequence of each oligonucleotide in each of the primers included in the primer library is known. For random priming as such is defined herein, sets of preparations of primers or primer combinations may be used. All the sequences in such sets are known. Each sample of primer or primer combination taken from the primer library to be used to prime DNA synthesis in the initial steps of the sequencing methods described herein comprises only a portion of a single preparation, and different portions of the single preparation of the primer contained in the primer library are used to prime DNA synthesis in different nucleic acid molecules.

STATISTICAL ANALYSIS OF OLIGONUCLEOTIDE PRIMING

The present invention is based on a consideration of the statistics of the priming of enzymatic DNA synthesis as applied to nucleotide sequencing. Primers in the enzymatic sequencing method are typically oligodeoxyribonucleotides. However, oligoribonucloetides, oligoribonucleotides containing methylphosphonate bonds, and perhaps other types of linkages of normal DNA or RNA bases, or bases such as inosine, 5-bromouracil, or other modified bases that are not normally found in DNA or RNA, can also associate specifically with template nucleic acids and prime sequencing reactions, as can such linkages of bases which are themselves linked to various reporter groups such as fluorescent tags, biotin etc.

In this specification, the terms primer or oligonucleotide are meant to specify a molecule containing a defined sequence of bases linked together in such a way that said molecule is capable of specific association according to known base pairing rules with a sequence of bases in the template nucleic acid, and is capable of priming DNA synthesis reactions suitable for nucleotide sequencing. The terms hexamer, heptamer, octamer, nonamer and decamer are meant to refer specifically to primers of length 6, 7, 8, 9 and 10 bases, respectively. The nucleic acid to be sequenced may be referred to for convenience as DNA, but it should be understood that this is only for convenience and that the invention applies to single-stranded or double-stranded DNA molecules or to single-stranded or double-stranded RNA molecules. A primer that primes at one and only one site in a nucleic acid molecule may be referred to as a unique primer for that molecule and the priming site as a unique priming site in that molecule.

In the statistical analysis of priming, which provides the basis for the present invention, important parameters are the length of the primer, p, and the total length of the nucleic acid to be sequenced, T. The length of the primer is the number of bases in the primer molecule that are capable of specific base pairing with the template nucleic acid. For a single-stranded nucleic acid, T=L, where L is the number of bases in the chain. For a double-stranded nucleic acid having complementary strands of equal length, T=2L, where L is again the number of bases in a single chain, which also equals the number of base pairs. For substantially equimolar mixtures of different nucleic acid chains, including double-stranded nucleic acids having complementary strands of unequal length, T=ΣL, the sum of the numbers of bases in the individual chains. For mixtures of the type that would be equivalent to random breakage of a unique molecule, T is the total number of bases that would have been in the unique molecule.

In the statistical analysis, it is assumed that primers of arbitrary length prime DNA synthesis at every perfectly complementary sequence in a template nucleic acid molecule but at no other sequence. The number of potential priming sites in the molecule is approximately equal to the total number of bases T. For a nucleic acid molecule of random sequence, the expected frequency of priming sites for a single randomly selected oligonucleotide is approximated by the Poisson distribution $$P(r) = \frac{n^r e^{-n}}{r!} \quad (1)$$

where $P(r)$ is the probability of having exactly r priming sites in the nucleic acid molecule and $n=T/4^p$ is the average number of priming sites for an individual oligonucleotide per nucleic acid molecule of length T, where $4^p$ is the number of different combinations of the four nucleotides that can form an oligonucleotide of length p.

Random Priming

Useful sequence information is obtained when DNA synthesis is primed at a single site in a nucleic acid molecule. For a nucleic acid molecule of essentially random sequence, the probability $P(1)$ that a randomly selected oligonucleotide will have a single priming site is a maximum of 0.368 when $n=1$ (Table 1). Attempts to prime sequencing reactions where it is not known whether or where a selected oligonucleotide will prime in the nucleic acid molecule are referred to in this specification as random priming. The term "random primer" refers to a primer used for random priming.

In practice, primers of length 6 or longer are used to prime sequencing reactions. By simple manipulations of equation 1 and the equation for n, it is easily shown that for single primers of length 6-10, a value of n between approximately 0.462 and 1.848, and an expected fraction of productive primings of sequencing reactions between 0.291 and 0.368, can be achieved for any single-stranded nucleic acid of length between approximately 1900 and 1,938,000 bases or any double-stranded nucleic acid of length between approximately 950 and 969,000 base pairs. This is illustrated by the figures shown in Table 1, which are rounded off from the exact calculations. For example, the largest double-stranded molecule for which $P(1)$ stays above 0.291 with octamer primers is approximately 60,600 base pairs, which is the same size as the smallest molecule for which $P(1)$ stays above 0.291 with nonamer primers.

The minimum fraction of productive primings can be increased by using a mixture of two or three primers of the same length. Mixtures of more than one primer, lo all of which have the same length, are referred to in this specification as primer combinations. Increasing the number of primers in the combination decreases the length of nucleic acid that has a given value of $P(1)$, and the decrease in length is in the same ratio as the increase in number of primers. For example, doubling the number of primers provides the same value of $P(1)$ for a nucleic acid half the length, quadrupling the number of primers provides the same value of $P(1)$ for a molecule one-fourth the length, etc.

By the use of single primers or two-primer combinations with primer lengths in the range of 6 to 10, the value of n can be maintained between approximately 0.693 and 1.386, and the expected frequency of productive primings can be maintained between 0.347 and 0.368, for single-stranded molecules between about 1420 and 1,454,000 bases or for double-stranded molecules between about 710 and 727,000 base pairs. Again to illustrate from Table 1, the largest molecule for which $P(1)$ stays above 0.347 with an octamer primer is 45,400 base pairs. The smallest molecule for which $P(1)$ stays above 0.347 with a single nonamer primer is twice this size, 90,900 base pairs, but a combination of two nonamers produces the same value of P(1) for a molecule half the size, which is the same length molecule as the maximum for octamers.

Extending this analysis, single primers, two-primer combinations, or three-primer combinations with primer lengths in the range of 6 to 10 can maintain the value of n between approximately 0.863 and 1.151, and the expected frequency of productive primings between 0.364 and 0.368, for single-stranded molecules between about 1180 and 1,206,000 bases or for double-stranded molecules between about 590 and 603,000 base pairs. Again to illustrate from Table 1, the largest molecule for which P(1) stays above 0.364 with an octamer primer is 37,700 base pairs. The smallest molecule for which P(1) stays above 0.364 with a single nonamer primer is 113,000 base pairs, but a combination of three nonamers produces the same value of P(1) for a molecule one-third the size, which is the same length molecule as the maximum for octamers.

Primer combinations containing more than three primers may also be used, applying the same principles. For example, a single octamer, a combination of four nonamers, and a combination of 16 decamers all would have the maximum fraction of productive primings with a double-stranded molecule of 32,800 base pairs (Table 1), as would combinations of 64 primers of length 11 bases, 256 of length 12 bases, or 1024 of length 13 bases. The use of primer combinations extends the useful range of random priming for a given nucleic acid molecule to longer primers, which might have advantages in some situations. For example, longer primers would be expected to have a higher temperature optimum for priming sequencing reactions.

When using primer combinations, multiple priming may result from unique priming by more than one primer in the combination. In such cases, sequence information can be obtained by priming with individual primers from the combination. The frequency of obtaining sequence information from such individual primers may be higher than from further random primings, depending on the average number of priming sites and the number of primers in the combination.

The above principles allow the method of random priming to be applied to any nucleic acid molecules that can be analyzed by primed sequencing techniques. The size ranges given in the above examples are not intended to limit the invention. The random priming method can also be applied with any primers suitable for primed sequencing techniques, including primers longer than 10 and potentially even those shorter than 6. When referring to random priming, the terms primer and priming are understood to include the possibility of both single primers and primer combinations unless stated otherwise.

Directed priming

If the sequence of part of a nucleic acid molecule is known, a primer that has a single priming site in the known sequence can be used for priming sequencing reactions. Priming in situations where the primer is known to have a single priming site within the known sequence is referred to in this specification as directed priming. The term "directed primer" refers to a primer used for directed priming. The probability that such a primer will have only a single priming site in the entire molecule, and will therefore provide useful sequence information, is the probability P(0) that no priming site occurs in the unknown sequence. The value of P(0) is given by equation i and depends on the lengths of both the unknown sequence and the primer.

SEQUENCING STRATEGY

Oligodeoxyribonucleotides of any desired nucleotide sequence can be synthesized readily by standard techniques with commercially available instruments or can be purchased from companies that make them to order (for example, from Genetic Designs, Inc., Houston, Tex.). Typical preparations yield 0.2–10 $\mu$mole of primer. A sequencing reaction typically requires about 1 pmole of primer, so each preparation of primer would contain enough material to prime $2 \times 10^5$ to $10^7$ separate sequencing reactions.

The improvement and efficiency in the method of the invention over conventional methods should be noted. In the conventional directed priming method, where known sequence is extended from a newly synthesized primer that primes near the end of the known sequence, primers are typically of length 16 bases or longer and therefore can be used only once for an amount of sequence equivalent to the entire human genome. The methods of this invention use statistical analysis to select primers of lengths that allow repeated use of primers from the same preparation and therefore have the potential to lower the cost of primers relative to the amount of sequence obtained by a factor of $10^5$ or more, depending on the volume of sequencing. The methods will be illustrated with cosmid DNAs such as might be used for sequencing the human genome.

A typical cosmid DNA might contain 5,000 base pairs of vector DNA and 40,000 base pairs of cloned DNA. The probabilities that randomly selected primers of lengths 6–12 will have no priming site, exactly one priming site, or more than one priming site in such a DNA molecule are given in Table 2. Clearly, hexamers and heptamers are too small to have much chance of priming useful sequence information in such a cosmid molecule. Libraries of octamers, nonamers or decamers, on the other hand, could generate sequence information quite efficiently from large numbers of different cosmid DNAs.

Combined random and directed priming

In a preferred embodiment of the invention, the sequencing strategy combines random and directed priming. Initial blocks of sequence are generated by random priming and these sequences are then extended by directed priming until they merge. FIG. 1 provides a diagrammatic summary of this strategy.

Random priming phase

In the first stage, random priming with single octamers would provide sequence information in a fraction of sequencing reactions equal to 0.348, the value of P(1) for the cosmid DNAs. The fraction of productive reactions primed by single nonamers is expected to be only 0.244, but combinations of 2 nonamers increase this to 0.346 and combinations of 3 nonamers to 0.368. The fraction of productive reactions would also be 0.368 when priming is with combinations of 12 decamers. Thus, the random priming phase is expected to generate sequence information in slightly more than one of three sequencing reactions.

With current technology, each successful set of sequencing reactions determines the sequence of several hundred nucleotides. For purposes of illustration, it will be assumed in this specification that an average of 500 nucleotides of sequence is obtained from each successful priming. It should be recognized, however, that the same methods apply when the average lengths of sequence obtained per priming are shorter or longer than 500. Of course, the longer the block of sequence obtained from each priming the more efficient will be the sequencing process.

In the random phase, different primers can be used individually and sequentially or in sets of sequencing reactions that are prepared and analyzed in parallel. Different sets can themselves be analyzed sequentially. When priming is done sequentially, succeeding primers or sets of primers are preferably selected to exclude any that would prime within the previously determined sequence. In this way, the priming is restricted to the unknown portion of the molecule. Which of the embodiments is preferred depends on the specifics of the sequencing program. In some high volume situations it may be more economical to prime each DNA individually and sequentially with one primer or primer combination at a time, although many different DNAs would probably be analyzed in parallel. On the other hand, where the complete sequence of a single cosmid or other nucleic acid is desired in the shortest possible period, it is preferable to perform a set of randomly primed reactions in parallel to start the sequencing process.

An advantage of the random priming method is that the same set of primers can be used repeatedly to determine sequences in many different DNAs. What is meant by repeated use of a primer is that many different samples from the same preparation of primer are used in many different sequencing reactions In this specification, the term "set" as applied to primers, refers to a group of primers used repeatedly for random priming of many different DNAs. This is to distinguish "set" from the broader term "library" which is meant to apply to a collection of primers that is used repeatedly for directed priming or for both random and directed priming. Libraries would usually be larger than sets, in which case many different sets could be assembled from the primers in a library.

In random priming, each successful reaction should produce at least about 500 nucleotides of sequence, and these blocks of sequence should be distributed at essentially random positions in the DNA molecule. For cosmid DNAs, the first 10 blocks of randomly primed sequence are expected to have an average of about one overlap. Because cosmid DNAs are double stranded, the sequence of the complement of each block of sequence can also be inferred.

In cosmid DNAs, as in any double-stranded nucleic acid, the complement of any primer that is unique in the molecule will also be unique. The primer complement will prime at the same site but will direct DNA synthesis to the complementary strand and will extend the initial block of sequence in the opposite direction. Therefore, each of the initial blocks of randomly primed sequence can be extended at least about 500 base pairs in the opposite direction. Because of the difficulty in reading nucleotide sequence close to the primer, there will probably be a short gap between the two blocks of base pairs of sequence; however, the location of the gap is known and such gaps are easily closed when the confirmatory sequences of the complementary strands are determined by directed priming.

For initiating the sequence of cosmid DNAs by random priming, a set of 30 primers and their complements are expected to generate perhaps 20–25% of the sequence in 8–11 blocks of about 1000 base pairs each. The same set of primers could be used repeatedly to initiate the sequence of many different cosmid DNAs. In each cosmid DNA, about the same fraction of the 30 initial primers is expected to prime uniquely, but the subset of primers that is unique will normally be different for each DNA molecule and the blocks of sequence will normally also be different, unless the cosmid DNAs overlapped in the genomic DNA from which the cosmids were derived, or unless the priming site is located in a repeated portion of the genome.

The primers in the set used to initiate sequencing by random priming can be selected so as to optimize their usefulness for determining the sequence of a particular set of nucleic acids. Although it has been assumed that the nucleotide sequence is essentially random in the nucleic acids to be sequenced, the statistical analyis can be modified by well known techniques to take into account known deviations from randomness. For example, the DNA is often known to be enriched in AT or GC base pairs, and mammalian DNAs are known to have a strong bias against the dinucleotide sequence CG, with clustering of the CG sequences that are present. For some genomes the nucleotide sequences of highly or moderately repeated elements are known. The sequence of the vector portion that would be present in each cosmid DNA derived from the same cosmid vector would also be known or easily determined. The primers in a set used for random sequencing might for example exclude any that would prime in the vector portion of the cosmids or in known repeated elements of the genome, and might be chosen to reflect the average base composition and known dinucleotide biases of the genome being sequenced. These are examples of the types of optimization that is possible. Primer selection in individual cases could be optimized according to what is known about the nucleic acid being sequenced and the specific goals of the sequencing project.

The initial blocks of sequence provided by random priming give a unique signature to each cosmid DNA being sequenced. When the same set is used to prime each cosmid DNA, these initial blocks of sequence are useful for comparing different cosmids with each other and with emerging blocks of genomic sequence to detect overlaps. In a large scale genome sequencing project, it might be more efficient to use the initial blocks of randomly primed sequence to establish overlaps between cosmids rather than to make the independent effort to order the cosmid DNAs by other means before sequencing them. Such a signature provides a great deal more information than almost any other mapping method, and in a high volume sequencing facility would be easy to obtain. Where some but not all blocks of randomly primed sequence overlap with known sequence, the remainder of the known portion of the cosmid does not have to be sequenced further, and knowledge of that sequence improves the efficiency of determining the sequence of the unknown portion by directed priming.

Random priming could be continued through many steps within the same molecule, each succeeding step excluding primers that would prime within the sequence previously known or determined. This strategy could be carried forward until a large fraction or all of the sequence had been determined, and gaps could be filled by directed priming. However, the most efficient strategy would be to switch from random to directed priming after only as much sequence is determined that the probability of obtaining sequence information by directed priming is equal to or greater than the probability of obtaining sequence information by random priming.

The number of primers convenient to have in a set for random priming will depend on factors such as the size of the nucleic acids being sequenced and the number of sequencing reactions that can conveniently be analyzed at the same time. In some situations, random priming of many different nucleic acids with only a single primer or sets of 2, 3 or 4 primers will be an efficient strategy. Sets of 5–10 primers would be likely to produce at least one block of unique sequence in most molecules. For cosmid DNAs, a set of approximately 30 primers should typically produce about 8–11 independent blocks of sequence with perhaps one overlap. Larger sets of primers will produce proportionately more blocks of sequence but also more overlaps, which decrease the sequencing efficiency. Nevertheless, in some situations more blocks of sequence may be needed and a higher number of overlaps can be tolerated, so that sets of as many as 50, 100, 200 or more primers may be useful. Larger sets of primers would also provide more blocks of sequence but still a small number of overlaps when initiating the sequencing of nucleic acids larger than cosmid DNAs, such as large viral DNAs or yeast artificial chromosomes, for example. In situations where multiplexing can be used, sets of 50 to 500 primers might be useful. Of course for double-stranded nucleic acids, sets of pairs of complementary primers may be used. It seems unlikely that sets containing more than 1000 primers or pairs of complementary primers would be needed for most random priming applications.

Directed priming phase

The probability that directed priming will be unique in the molecule is the probability $P(0)$ that no priming site for a primer that has a unique priming site in the known sequence will occur in the unknown sequence. This probability depends on the length of unknown sequence and on the length of the primer. These probabilities are given in Table 3 for different lengths of unknown sequence when priming is by a single octamer, nonamer or decamer.

In constrast to their usefulness in random priming, primer combinations are disadvantageous for directed priming. When referring to directed priming in this specification, the terms primer and priming are understood to refer to a single primer that has a unique priming site in the known sequence of the nucleic acid molecule being sequenced.

Directed priming can be used to extend any blocks of nucleotide sequence whose sequences are known or are determined by random priming or by some other technique such as application of chemical sequencing methods to end-labeled fragments. The important distinction between directed priming as taught by this invention and previously used priming methods is that the primers used in this invention have a lower probability of priming uniquely in a given molecule but have a high enough probability of priming that they can be used repeatedly to prime sequencing reactions in many different molecules. This property permits libraries of primers to be established or accumulated that are sufficient to complete the sequence of almost any cosmid DNA.

The probability that directed priming will be successful increases with the length of the primer. This probability also increases as the amount of sequence remaining to be determined in the molecule decreases. For example, if a switch from random to directed priming is made at the point where 30,000 base pairs of cosmid DNA sequence remains unknown, the probability of unique priming by an octamer is 0.400, by a nonamer is 0.795 and by a decamer is 0.944. As directed priming proceeds and less and less of the sequence remains unknown, the probability of successful priming increases (Table 3). The choice of whether octamers, nonamers, decamers, or longer primers should be used will depend to some extent on the costs of performing and analyzing sequencing reactions relative to the costs of accumulating a primer library that is sufficiently efficient for determining nucleotide sequences. An analysis of the efficiency of primer libraries is presented below.

Combined strategy

In a combined random and directed priming strategy for determining the entire sequence of a cosmid DNA, sequencing may, for example, be initiated by random priming with a set of 30 primers. Each of the initial blocks of sequence is extended in the opposite direction by priming with the complement of the unique primers or primer combinations. These initial 10 or so blocks of sequence are then extended in both directions by directed priming until all blocks of sequence merge. In most cases the sequence of the vector portion of the DNA is known, so that primers that prime within the vector portion of the DNA are excluded, except for directed priming from the ends of the known vector sequence into the unknown cloned DNA. The initial sequence is determined on one of the two complementary strands, although not the same strand throughout the entire molecule. The confirmatory sequences on the other strand, plus the small gaps where complementary primers had initiated sequence in both directions, can then be completed by directed priming that will be almost 100% successful, since almost the entire sequence of the molecule will be known. The steps of such a strategy are diagrammed in FIG. 1.

The combined random and directed priming strategy may be applied not only to cosmid DNAs but also to any linear or circular double-stranded nucleic acid, whether the sequence is completely unknown or partly known. The strategy will also be successful in determining the complete sequence of circular single-stranded nucleic acids, although of course priming with the complements of the original set of random primers would not be used as a routine step with any single-stranded nucleic acids. For linear single-stranded nucleic acids, random priming will not be likely to occur near the 3' end of the molecule. To complete the sequence of these molecules, the sequence at the 3' end would need to be determined by, for example, chemical sequencing techniques and then extended by directed priming until it links with the sequence determined from the closest random priming.

These random and directed priming methods apply to any nucleic acids that are suitable for primed sequencing, whether cloned or not cloned. Such nucleic acids could include, for example, viral nucleic acids, cDNAs, DNA or RNA that has been amplified by polymerase chain reaction or related techniques from simple or complex mixtures of nucleic acids, or any nucleic acid that can be isolated in a preparation that is homogeneous enough to determine nucleotide sequences. These methods could be particularly useful for direct sequencing of viral nucleic acids whose sequences are completely unknown. Random priming itself, using an appropriate set of primers, could provide rapid and specific identification of viral nucleic acids from the initial blocks of sequence obtained, and might be useful as a diagnostic technique.

As with any sequencing project, computers may be used in accumulating and maintaining sequence information. Computer programs may also be adapted or created specifically for use with these methods. In a genome sequencing project, initial blocks of sequence produced by random priming are compared to each other and to the emerging genomic sequence to identify overlaps. A computer is conveniently used to select primers for extending sequences in a given nucleic acid and to identify overlaps when blocks of sequence merge. Inventory and maintenance of large libraries of primers also benefit from special programs.

Relative numbers of sequencing reactions needed

The probabilities of unique priming in the random and directed priming phases can be used to estimate the numbers of sequence reactions needed to determine the entire sequence of nucleotides to be sequenced relative to the minimum number of sequence reactions needed to confirm the entire sequence by directed priming when the entire sequence is known. For purposes of illustration, it will be assumed that the nucleotides to be sequenced contain 40,000 base pairs of DNA cloned in a cosmid. It will be further assumed that the sequence of the vector portion of the cosmid DNA is known, and that a set of sequencing reactions determines, on average, the sequence of 500 nucleotides. In this analysis, the minimum overlap needed to extend a sequence by directed priming is ignored. Table 4 summarizes the average numbers of sequencing reactions required by a combined random and directed priming strategy, where the switch from random to directed priming is made after 10,000 base pairs of sequence is determined, or by a completely directed priming strategy, using octamer, nonamer or decamer primers.

If the sequence were completely known, 80 sets of sequencing reactions would be required to determine the entire sequence on one of the two complementary strands by directed priming and another 80 sets to determine the confirmatory sequence of the complementary strand. With a combined random and directed strategy, making allowance for redundant sequencing when known blocks of sequence merge, and assuming that unique primers within the vector sequence are used to direct sequencing into the ends of the cloned DNA, an average of 161 sets would be required to complete the sequence on one of the two strands (but not the same strand throughout the molecule) when directed priming is by octamers, 117 when by nonamers, and 109 when by decamers. At this stage, essentially the entire sequence is known, so the confirmatory sequences on the complementary strand and the filling in of the short gaps at the positions of the random primers would require only the minimum number of directed primings, or perhaps a few extra primings, depending on the spacing of the random priming sites in the molecule. Assuming the confirmatory sequences can be completed in the required minimum of 80 sets, the entire sequence of both strands could be completed in an average of about 1.51, 1.23 or 1.18 times the minimum of 160 sets required, using octamers, nonamers or decamers, respectively.

Entirely directed priming, starting from within the vector portion of the cosmid and proceeding sequentially along each strand, would be somewhat more efficient than a combination of random and directed priming. An average of 153 sets of sequencing reactions primed by octamers, 93 by nonamers, or 83 by decamers would be required to complete the sequence of the first strand, compared with the required minimum of 80; completion of both strands would require 1.46, 1.08 or 1.02 times the required minimum of 160 sets.

When applying the random and directed priming methods of this invention to current methods for determining nucleotide sequence, a significant fraction of the total effort and expense will be devoted to analyzing the products of sequencing reactions by gel electrophoresis. A simple, convenient and reliable test for distinguishing whether DNA synthesis had been primed at zero, one, or more than one site in sequencing reactions therefore improves the efficiency of the sequencing process by eliminating the need for gel electrophoresis of samples that will not give useful sequence information. Such a test is based, for example, on the yield of acid-precipitable or hybridizable radioactivity or fluorescence and is particularly useful for increasing the efficiency of random priming, which can provide useful sequence information in a maximum of 37% of reactions. With such a test, random priming with even rather unfavorable statistics is made relatively efficient, if more appropriate primers are not available. If productive sequencing reactions constituting as few as 5% of the total reactions are detected reliably, primers having an average number of priming sites per molecule ranging between 0.05 and 4.50 could be useful for random priming (Table 1).

Advantages over random cloning methods

With the sequencing methods taught by this invention, the amount of effort required to obtain sequence information decreases as more of the sequence becomes known, and the excess number of sequencing reactions needed above the minimum can be as small as a few percent. In contrast, the effort in random cloning methods increases as more of the sequence becomes known, and the excess number of sequencing reactions required is of the order of several fold to tenfold. Furthermore, sequencing as taught by this invention could potentially be done on a single preparation of DNA, and the considerable cost and effort of subcloning, preparing multiple DNA samples, or mapping fragments is eliminated.

PRIMER LIBRARIES

The number of primers needed in a primer library in order that almost any nucleic acid of a given length or smaller could be sequenced entirely by priming with primers contained in the library depends on the efficiency of sequencing that is desirable or acceptable. If the effort or cost of assembling and maintaining a primer library were negligible, complete libraries containing all $4^p$ possible primers of length p would be the most efficient. A complete library of octamers has 65,536 primers; a complete library of nonamers has 262,144 primers; and a complete library of decamers has 1,048,576 primers (see Table 2). However, the statistical analysis below teaches how to compare the sequencing efficiencies of primer libraries of different sizes as applied to nucleic acids of different lengths, and shows that substantially smaller libraries can be very efficient for sequencing. A principal advantage of the present method is that complete libraries of primers are not necessary for efficient sequencing.

In this specification, the size of a library refers to the number of primers contained in the library. For ease of discussion, the statistical treatment and examples deal with libraries in which primers are all of the same length. However, libraries that contain primers of different lengths would also be useful in this invention, and their efficiencies could be estimated by obvious extensions of the statistical analysis.

The sequencing efficiency of a primer library depends on the density of unique priming sites represented in the library. If, for example, about 500 nucleotides of sequence can be determined from a set of sequencing reactions, a unique primer must be available within a considerably smaller interval in order to be able to extend known sequences efficiently. The density of unique priming sites for octamers, nonamers and decamers in DNA the size of a cosmid is high enough that priming from a complete library would allow any known sequence to be extended with little overlap. Reducing library size increases the average overlap needed to extend known sequences, because the primer that would initiate synthesis with minimal overlap may not be present in the library. Any increase beyond the necessary minimum overlap will decrease the amount of new sequence that can be obtained from a set of sequencing reactions.

The probability $P(x)$ that a library of oligonucleotides will contain no primer that initiates DNA synthesis uniquely within an interval of x nucleotides in a DNA molecule is $$P(x) = [1 - P(s)\, P(0)]^x \qquad (2)$$

where $P(S)$ is the probability that an oligonucleotide that primes at a particular site will be found in the library, and $P(0)$ is the probability that the selected primer will be unique in the entire DNA molecule. For a library of oligonucleotides of length p, $P(S)$ is simply the number of oligonucleotides in the library divided by $4^p$, the total possible number; $P(0)$ is given by the Poisson distribution (equation 1) and is a function of both the length of the DNA molecule and the length of the primer.

Two quantities derived from the above expression are useful for estimating and comparing efficiencies of libraries for sequencing nucleic acids of a given length, the 90% priming interval, $x_{90}$, and the average priming interval, $x_{avg}$. The 90% priming interval is the nucleotide length in a nucleic acid of a given length within which the library has a 90% chance of having a primer that initiates uniquely, and is calculated from equation 2 (where $P(x) = 0.1$). This length provides a convenient estimate of the longest overlap likely to be needed to extend a known sequence, since a library has a 99% chance of priming uniquely within twice the 90% interval, a 99.9% chance within three times the 90% interval, etc.

The average priming interval, on the other hand, is the average nucleotide length needed to reach the first useful priming site represented in the library and is given by $$x_{avg} = (x-1)\,[P(x-1) - P(x)] = \frac{1}{P(S)\,P(0)} - 1 \qquad (3)$$

This is the average reduction in new sequence obtained per reaction set when the library is used to extend known sequences.

The efficiency of a given library for extending known sequences by directed priming depends on the ratio of the average priming interval to the average length of sequence determined from a single priming site by whatever method of sequence analysis is used. A ratio of 1:100 or lower means that the average reduction in new sequence obtained per reaction set, referred to here as the overlap penalty, will be 1% or less, so sequencing will be very efficient. Ratios of 1:50 or 1:20 are also quite efficient, having an overlap penalty of only 2% of 5%. At ratios of 1:10 or 1:5, the overlap penalty is 10% or 20% and the loss of efficiency becomes more significant. At a ratio of 1:2.5, the loss of efficiency is quite serious, and at a ratio of 1:1, most sequences will not be able to be extended by use of primers found in the library.

Primer libraries for sequencing cosmid DNAs

If a typical set of sequencing reactions produces an average of 500 nucleotides of sequence from a single priming site, libraries having average priming intervals of 5, 10, 25, 50, 100, 200 and 500 would correspond to those discussed in the preceding paragraph. The library sizes of octamers, nonamers and decamers needed to achieve these average priming intervals in double-stranded DNAs 45,000 base pairs long, the size of cosmid DNAs, are given in Table 5. Also shown in Table 5 are the average priming intervals of the complete libraries and the 90% priming intervals for all of the libraries. The figures given in Table 5 show that complete libraries would be very efficient for sequencing cosmid DNAs, but that much smaller libraries still give reasonable sequencing efficiencies.

The 90% priming interval gives a measure of how frequently a primer that is not present in the library will be needed to extend a sequence. For the examples in Table 5, libraries with an average priming interval of 50, corresponding to an overlap penalty of 10%, have a 90% priming interval of 116. Therefore, in fewer than 1% of cases will the increased overlap be longer than 232 nucleotides, and primers in addition to those available from the library would be needed only occasionally. Libraries with an average priming interval of 100 would have an overlap penalty of about 20%, and 10% of sequence extensions would require an overlap of longer than 231 nucleotides and therefore would probably require a primer that is not present in the library. For libraries with an average priming interval of 200, about 30% of cases might be expected to need additional primers, and for libraries with an average priming interval of 500, the majority of cases would require primers not available from the library.

The above analysis suggests that relatively small libraries of octamers, nonamers or decamers can be very useful for sequencing cosmid DNAs. As few as 1,287 octamers, 1,838 nonamers, or 5,684 decamers would allow sequences to be determined with about a 40% overlap penalty and the necessity to synthesize additional primers for perhaps 30% of sequencing reactions. As few as 2,588 octamers, 3,659 nonamers or 11,312 decamers would allow sequences to be determined with about a 20% overlap penalty and the necessity to synthesize additional primers for perhaps 10% of sequencing reactions. As few as 5,074 octamers, 7,246 nonamers or 22,403 decamers would allow sequences to be determined with about a 10% overlap penalty and only an occasional need to synthesize additional primers. As few as 9,952 octamers, 14,212 nonamers or 43,944 decamers would allow sequences to be determined with only a 5% overlap penalty, and, in almost all cases, without the need for additional primers. As few as 23,523 octamers, 33,593 nonamers or 103,868 decamers would allow sequences to be determined with only a 2% overlap penalty, and as few as 43,126 octamers, 61,587 nonamers or 190,425 decamers would reduce the overlap penalty to 1%.

To have an equivalent priming density for cosmid DNAs, a library need contain only about 43% more nonamers than octamers but more than threefold more decamers than nonamers, the difference reflecting the effect of $P(0)$. Equivalent priming densities with even longer primers require about a fourfold increase in library size for each additional nucleotide of primer length. Nonamers may be the preferred length of oligonucleotide for sequencing cosmid DNAs, since a relatively modest increase in library size over octamers provides a substantial reduction in the number of sequencing reactions needed (Table 4). The much more substantial increase in size needed for a decamer library of equivalent priming density produces only a marginal further decrease in the number of sequencing reactions required (Table 4).

Primer libraries for sequencing other nucleic acids

The above examples have been developed for cosmid DNAs. Large numbers of cosmid DNAs will need to be sequenced for the human genome sequencing project, and this demand provides a rationale for assembling libraries useful for sequencing cosmids. However, such libraries would be even more efficient for sequencing nucleic acids smaller than cosmid DNAs. It is easily shown by use of equations 2 and 3 that the priming intervals decrease when a library of a given size is used for sequencing smaller nucleic acids, and $P(0)$, the probability that a given directed priming will provide unique sequence, increases. Therefore, a primer library suitable for sequencing cosmid DNAs would be suitable for the great majority of nucleic acids available for sequencing.

Libraries assembled for sequencing nucleic acids of a given size will often be useful for sequencing larger nucleic acids as well, although with a lower efficiency. For example, the combined random and directed priming strategy that will determine the sequence of a 45,000 − bp DNA in about 1.5 times the minimum number of sequencing reactions, using octamers (Table 4), could determine the sequence of DNAs as large as 180,000 base pairs, using nonamers, or DNAs as large as 720,000 base pairs, using decamers, also in about 1.5 times the minimum number of sequencing reactions. A library of 14,212 nonamers that has an average priming interval of 25 for cosmid DNAs (Table 5) would have an average priming interval of 71.8 and a 90% priming interval of 167 for DNAs of 180,000 base pairs. A library of 43,944 decamers that has a priming interval of 25 for cosmid DNAs (Table 5) would have an average priming interval of 32.6 and a 90% priming interval of 76.3 for DNAs of 180,000 base pairs, and would have an average priming interval of 93.2 and a 90% priming interval of 216 for DNAs of 720,000 base pairs.

Sequencing of double-stranded DNAs as large as cosmid DNAs by primed sequencing is clearly within the reach of current sequencing technology, as shown in Example 1. The upper limit of nucleic acid length for which primed sequencing can provide sequence information is not known. The longer the template the more of it is needed to provide an equivalent molar concentration of substrate for sequencing reactions, and this will provide a practical limit. For example, direct sequencing of the human genome would theoretically be possible with primers 16 bases long, but sequencing reactions comparable to those in Example 1 would require 600 mg of DNA at a concentration of 60 g/ml. The upper limit of nucleic acid length will depend ultimately on how sensitively the products of sequencing reactions can be detected. Of course, nucleic acids that are too large to sequence directly could be divided into lengths that can be sequenced, by cloning into cosmid vectors or other vectors, for example. In some cases, it might be advantageous to subclone large DNAs that could be sequenced directly in order to take advantage of an existing primer library.

The techniques of analysis described in this specification can be applied to estimate the sizes and compositions of libraries needed for a given efficiency of sequencing of any nucleic acids for which primed sequencing methods are suitable. In practice, optimum library size and composition will presumably reflect some balance between the costs of analyzing sequencing reactions or of adding more oligonucleotides to the library.

Establishment of libraries

An advantage of the sequencing methods outlined here is that useful libraries can be accumulated during the course of large scale sequencing projects. An extensive library of primers, and its attendant expense, need not be provided at the outset; primers for extending known sequences could be synthesized as required and deposited in the library. Initially, the cost of sequencing would be similar to that of conventional primer-based sequencing, but as the library increased, fewer new primers would have to be synthesized and the cost of sequencing would steadily decline.

Each preparation of a primer has so much sequencing capacity that portions of it can be distributed into many different libraries, each of which may have the same or different primers. Such libraries could contain as little of each primer as needed for a single sequencing reaction, or might contain amounts sufficient for any convenient number of primings. Libraries with large priming capacities would be useful in sequencing centers, and libraries with smaller priming capacities would be useful in individual laboratories. Because of the possibility of synthesizing enough primer for $10^7$ or more primings in a single preparation, libraries could probably be distributed quite economically. For example, an initial library could be divided into 1000 libraries each of which has a capacity for 10,000 primings with each primer. Such economical distribution to many laboratories may make it advantageous to prepare and distribute basic primer libraries to many sequencing centers rather than to accumulate them gradually in individual centers.

The primers in a library can be selected so as to optimize their usefulness for determining the sequence of a particular set of nucleotide molecules. Although it has been assumed that the nucleotide sequence is essentially random in the nucleic acids to be sequenced, the statistical analyis can be modified by well known techniques to take into account known deviations from randomness. For example, the DNA is often known to be enriched in AT or GC base pairs, and mammalian DNAs are known to have a strong bias against the dinucleotide sequence CG, with clustering of the CG sequences that are present. For some genomes the nucleotide sequences of highly or moderately repeated elements are known. The sequence of the vector portion that would be present in each cosmid DNA derived from the same cosmid vector would also be known or easily determined. The primers in a library might, for example, exclude any that would prime in the vector portion of the cosmids, and might be chosen to reflect the average base composition and known dinucleotide biases of the genome being sequenced. Primers convenient for sequencing known repeated elements in a genome being sequenced might also be included in the library. These are examples of the types of optimization that would be possible. Primer selection in individual cases could be optimized according to what is known about the nucleic acid being sequenced and the specific goals of the sequencing project.

PRIMED SEQUENCING REACTIONS

The success of primed sequencing methods in general, and of the random and directed priming methods taught by this invention in particular, requires selective priming of DNA synthesis at single sites in the nucleic acids being analyzed. Enzymes that are commonly used and commercially available for use in primed sequencing include T7 DNA polymerase, T7 DNA polymerase modified to reduce exonuclease activity, Klenow fragment of E. coli DNA polymerase, Taq DNA polymerase, AMV reverse transcriptase and M-MuLV reverse transcriptase. Primers are typically ligodeoxyribonucleotides or modified oligodeoxyribonucleotides, although other primers are also used. M. Smith, in his review titled "Synthetic oligodeoxyribonucleotides as probes for nucleic acids and as primers in sequence determination" (in "Methods of DNA and RNA Sequencing" edited by S M. Weissman, Praeger Publishers, New York, 1983), states on page 55, in reference to primed sequencing: "In general, oligodeoxyribonucleotide of 7 to 15 nucleotides work well in this type of experiment, the primary determinant of oligodeoxyribonucleotide length being that required to recognize a unique site on the target DNA." Commercially available primers for determining nucleotide sequence in commonly used cloning vectors are typically in the range of 15 to 31 nucleotides long.

A large body of work has described specific association between oligonucleotides and complementary sequences in longer nucleic acids. Such hybridization reactions are commonly used for specific identification and quantitation of nucleic acids in complex mixtures, as well as for primer-directed DNA synthesis. Clearly, oligonucleotides are capable of associating selectively with perfectly complementary sequences in complex mixtures of nucleic acids in preference to imperfectly complementary sequences, even those which would result in only a single mismatched base pair. On the other hand, oligonucleotides can also be made to prime DNA synthesis at imperfectly complementary sites, which is the basis for a large body of work on directed mutagenesis.

The random priming method described herein could tolerate a certain amount of priming at imperfectly complementary sites, as long as a suitable fraction of all sequencing reactions are primed predominately at a single site in the molecule being sequenced. However, the directed priming method requires that a substantial majority of priming in each sequencing reaction be at the selected site, which will be perfectly complementary to the primer. Therefore, the conditions used for sequencing reactions should be chosen so that the primer being used will prime predominately at perfectly complementary sites.

Factors known or likely to affect the selectivity of priming include the concentrations of primer, nucleic acid and polymerizing enzyme, the incubation temperature, and the ionic conditions, particularly the concentration of $Mg^{++}$ and the overall ionic strength. The presence of proteins such as E. coli ssb protein, T4 gene 32 protein or T7 gene 2.5 protein, which destabilize secondary structure in the template DNA, can improve the accessibility of the DNA to the primer. The presence of proteins that normally interact with the DNA polymerase in synthesizing DNA, such as the T7 gene 4 helicase-primase, might also be expected to improve selectivity of priming, as might the E. coli recA protein or other proteins that affect base pairing between nucleic acids. The conditions of any previous annealing reactions can also affect selectivity in a subsequent DNA synthesis reaction. When sequencing double-stranded nucleic acids, the conditions of annealing or sequencing should promote specific priming in preference to reassociation of the complementary strands. In some cases, random or specific fragmentation of the template nucleic acid might be helpful.

Even if primers are able to associate and prime at mismatched sequences in the template DNA, the rate of association and priming at perfectly complementary sites should be faster under most conditions. Reaction conditions that maximize such kinetic differences could also be employed, as disclosed in Example 2.

Ideally, the same reaction conditions would be used for all primers in a library. However, differences in stability or other factors may necessitate different reaction conditions for different primers in a library. Information useful for choosing appropriate reaction conditions might include, for example, the Tm for association of individual primers with DNA, which can be calculated from the primer length and nucleotide sequence (using rules given by Quartin & Wetmur, Biochemistry 28, 1040–1047 (1989), for example). The presence of a phosphate group on the 5' end of the primer might be expected to improve the selectivity for perfect priming over mismatched priming.

Some primers may be unsuitable for sequencing certain nucleic acids under any condition. For example, primers that are palindromes would not be useful for sequencing double-stranded DNA because if they prime at all they must prime at sites in both strands. Even if only a relatively small fraction of primers of a given length were found to be useful for primed sequencing, the random and directed priming methods described here could be useful, since relatively small libraries can provide very efficient sequencing.

EXAMPLE 1

T7 DNA, which was used as test DNA because its entire nucleotide sequence is known and its size is similar to a typical cosmid, was prepared from phage particles that had been purified by isopycnic centrifugation in CsCl solution: wild-type DNA was released from the phage particles by phenol extraction followed by chloroform extraction; T7 mutant X134 DNA was released by heating for 5 min at 65° C. in 10 mM $Na_3EDTA$ solution. Each DNA was precipitated with two volumes of 95% ethanol and redissolved in 10 mM Tris-Cl, 0.1 mM Na₃EDTA, pH 8.0 at a concentration of 800 μg/ml. To prepare sequencing reactions, 10 μl of DNA solution was heated for 3 min in a boiling water bath, placed on ice, and 1 μl containing 1 pmol of octamer primer (GGCCATTG) plus 2 μl of 200 mM Tris-Cl, pH 7.5, 100 mM MgCl₂, 250 mM NaCl were added. After 30 min on ice, the two-step sequencing protocol for sequencing with Sequenase (U.S. Biochemicals Corp.) was followed, except that the 5 min labeling reaction, using [α-$^{32}$P]dATP, was on ice rather than at room temperature. Electrophoresis was through a 0.4 mm thick 6% polyacrylamide gel, with two loadings.

After electrophoresis, the gel was soaked in 10% acetic acid, 12% methanol for 15 min and then dried under Vacuum before autoradiography. The autoradiogram is shown in FIG. 2. Priming extended rightward from nucleotide 3607 of T7 DNA; nucleotide numbers in T7 DNA are indicated in the figure (Dunn & Studier, J. Mol. Biol. 166, 477–535 (1983)). Mutant X134 DNA contains C to T mutations at nucleotides 3687 and 3854. These procedures also produce good sequence information with lambda DNA, using octamer primers unique in the lambda DNA sequence.

In conducting sequencing experiments of known DNA molecules according to Example 1, some octamer primers having a unique binding site on the DNA molecule did not give useful sequencing information.

EXAMPLE 2

Sequencing reactions were primed by an octamer (GCAGCCTG) known to be unique in T7 DNA. Perfect pairing with this octamer should prime sequence leftward from nucleotide 5184. Under the conditions given in example 1, priming was at more than one site, making it impossible to determine nucleotide sequence. Eliminating the 30 min incubation of primer and DNA on ice, and instead initiating the two-step sequencing protocol immediately after adding adding primer and buffer to the DNA, resulted in autoradiograms that gave unambiguous sequence proceeding from the perfectly paired priming site in T7 DNA. Apparently the 30 rain annealing step on ice allowed priming at mismatched sequences, which interfered with reading of the sequence from the perfectly paired priming site. When the annealing step was eliminated, the primer apparently associated with the perfectly paired site sufficiently faster than with the incorrect site(s) that almost all priming in the sequencing reactions was from the perfectly paired site.

TABLE 1

Priming probabilities for different values of n. and lengths of double-stranded DNA molecules for which single primers of different lengths provide the same values of n.

| 2L/4$^p$ = | Probability of having 0.1 or >1 priming sites in a DNA | | | Length of double-stranded DNA (L. in bp) primed by a single primer of length: | | | | |
|---|---|---|---|---|---|---|---|---|
| n | P(0) | P(1) | P(>1) | 6 | 7 | 8 | 9 | 10 |
| 0.05 | 0.951 | 0.048 | 0.001 | 100 | 410 | 1,640 | 6,600 | 26,200 |
| 0.0625 | 0.939 | 0.059 | 0.002 | 130 | 510 | 2,050 | 8,200 | 32,800 |
| 0.125 | 0.882 | 0.110 | 0.007 | 260 | 1,020 | 4,100 | 16,400 | 65,500 |
| 0.250 | 0.779 | 0.195 | 0.026 | 510 | 2,050 | 8,200 | 32,800 | 131,000 |
| 0.288 | 0.750 | 0.216 | 0.034 | 590 | 2,360 | 9,400 | 37,700 | 151,000 |
| 0.462 | 0.630 | 0.291 | 0.079 | 950 | 3,800 | 15,100 | 60,600 | 242,000 |
| 0.693 | 0.500 | 0.347 | 0.153 | 1,420 | 5,700 | 22,700 | 90,900 | 363,000 |
| 0.863 | 0.422 | 0.364 | 0.214 | 1,770 | 7,100 | 28,300 | 113,000 | 452,000 |
| 1.000 | 0.368 | 0.368 | 0.264 | 2,050 | 8,200 | 32,800 | 131,000 | 524,000 |
| 1.151 | 0.316 | 0.364 | 0.320 | 2,360 | 9,400 | 37,700 | 151,000 | 603,000 |
| 1.386 | 0.250 | 0.347 | 0.403 | 2,840 | 11,400 | 45,400 | 182,000 | 727,000 |
| 1.848 | 0.157 | 0.291 | 0.551 | 3,800 | 15,100 | 60,600 | 242,000 | 969,000 |
| 2.50 | 0.082 | 0.205 | 0.713 | 5,120 | 20,500 | 81,900 | 328,000 | 1,310,000 |
| 3.50 | 0.030 | 0.106 | 0.864 | 7,170 | 28,700 | 115,000 | 459,000 | 1,840,000 |
| 4.50 | 0.011 | 0.050 | 0.939 | 9,220 | 36,900 | 147,000 | 590,000 | 2,360,000 |

TABLE 2

Frequencies of priming sites in a 45,000-bp DNA for oligonucleotide primers of different lengths, assuming random nucleotide sequence and random selection of a primer.

| Primer length p | Total possible primers 4$^p$ | Average # sites per molecule 90,000/4$^p$ = n | Probability of 0, 1, or >1 priming sites per 45,000-bp DNA molecule | | |
|---|---|---|---|---|---|
| | | | P(0) | P(1) | P(>1) |
| 6 | 4,096 | 22.0 | <10$^{-9}$ | <10$^{-8}$ | 1.000 |
| 7 | 16,384 | 5.49 | 0.004 | 0.023 | 0.973 |
| 8 | 65,536 | 1.37 | 0.253 | 0.348 | 0.399 |
| 9 | 262,144 | 0.343 | 0.709 | 0.244 | 0.047 |
| 10 | 1,048,576 | 0.0858 | 0.918 | 0.079 | 0.003 |
| 11 | 4,194,304 | 0.0215 | 0.979 | 0.021 | <10$^{-3}$ |
| 12 | 16,777,216 | 0.00536 | 0.995 | 0.005 | <10$^{-4}$ |

TABLE 3

Probabilities, P(0), of having no priming sites for an octamer, nonamer or decamer in different lengths of unknown double- stranded nucleotide sequence.

| Length of unknown sequence = L (bp) | Probability P(0) of no priming site for an | | |
|---|---|---|---|
| | octamer | nonamer | decamer |
| 45,000 | 0.253 | 0.709 | 0.918 |
| 40,000 | 0.295 | 0.737 | 0.927 |
| 35,000 | 0.344 | 0.766 | 0.935 |
| 30,000 | 0.400 | 0.795 | 0.944 |
| 25,000 | 0.466 | 0.826 | 0.953 |
| 20,000 | 0.543 | 0.858 | 0.963 |
| 15,000 | 0.633 | 0.892 | 0.971 |
| 10,000 | 0.737 | 0.927 | 0.981 |
| 5,000 | 0.858 | 0.963 | 0.991 |

TABLE 4

Average numbers of sets of sequencing reactions needed to complete the nucleotide sequence of a cosmid DNA consisting of 40,000 bp of unknown sequence and 5,000 bp of known vector sequence, assuming 500 nucleotides of sequence is obtained from each set of productive sequencing reactions, and assuming a strategy of: 1) random priming with octamers, followed by directed priming with octamers, nonamers or decamers after 25% of the sequence has been determined, or 2) completely directed priming with octamers, nonamers or decamers. Priming from within the vector sequence is assumed to be unique.

|  | Sets of sequencing reactions | | | |
|---|---|---|---|---|
|  | Minimum possible | Primers of length | | |
|  |  | 8 | 9 | 10 |
| Random and directed priming | | | | |
| Priming from vector | 2 | 2 | | |
| Random priming | 9 | 25.9 | | |
| Complementary priming | 9 | 9 | | |
| Directed priming (10,000 bp): | | | | |
| 30,000 bp unknown | 20 | 50.0 | 25.2 | 21.2 |
| 20,000 bp unknown | 20 | 36.8 | 23.3 | 20.8 |
| 10,000 bp unknown | 20 | 27.1 | 21.6 | 20.4 |
| Overlaps |  | 10 | 10 | 10 |
| First strand total | 80 | 160.8 | 117.0 | 109.3 |
| Complement | 80 | 80 | 80 | 80 |
| Both strands | 160 | 240.8 | 197.0 | 189.3 |
| Ratio | 1.00 | 1.51 | 1.23 | 1.18 |
| Completely directed priming | | | | |
| Priming from vector | 2 | 2 | 2 | 2 |
| Rest of first strand | 78 | 151.1 | 91.0 | 81.0 |
| Complement | 80 | 80 | 80 | 80 |
| Both strands | 160 | 233.1 | 173.0 | 163.0 |
| Ratio | 1.00 | 1.46 | 1.08 | 1.02 |

TABLE 5

Priming intervals in 45,000-bp DNAs with different sized libraries of octamers, nonamers or decamers.

| Priming interval | | Library size | | |
|---|---|---|---|---|
| $x_{avg}$ | $x_{90}$ | octamers | nonamers | decamers |
| 0.09 | 0.92 |  |  | 1,048,576 |
| 0.41 | 1.86 |  | 262,144 |  |
| 2.95 | 7.88 | 65,636 |  |  |
| 5 | 12.6 | 43,126 | 61,587 | 190,425 |
| 10 | 24.2 | 23,523 | 33,593 | 103,868 |
| 25 | 58.7 | 9,952 | 14,212 | 43,944 |
| 50 | 116 | 5,074 | 7,246 | 22,403 |
| 100 | 231 | 2,588 | 3,659 | 11,312 |
| 200 | 462 | 1,287 | 1,838 | 5,684 |
| 500 | 1,152 | 516 | 738 | 2,281 |

Sequencing Conditions

The nucleic acid molecule sequenced may be a long DNA molecule, such as viral DNA or a chromosome. More typically, nucleic acid molecules to be sequenced are fragments of larger molecules cloned into a suitable vector.

Any vector that is stable in a host cell, preferably a bacterial cell, can be used. Preferably, the vector can be replicated in the host cell.

The vector may be linear or cyclic; single-stranded or double-stranded. Some examples of single-stranded vectors include natural or synthetic plasmids as well as filamentous coliphages such as M13, f1 and fd. Some examples of double-stranded vectors include phage lambda, cosmids, others.

A double-stranded vector that is particularly suitable for large scale cloning is the cosmid, which is derived from phage lambda; Gene 4, 85–107 (1978), Proc. Nat. Acad. Sci. USA, 75, 4242–4246 (1979). Cosmid DNA has approximately 37,000–52,000 base pairs, of which, approximately 5,000 base pairs come from phage lambda. This leaves 32,000–47,000 base pairs of DNA of unknown sequence that can be inserted into the cosmid.

The nucleic acid molecule being sequenced must be single-stranded to be primed. If the nucleic acid molecule is double-stranded, the molecule is denatured by methods well known in the art. For example, one may use heat or the alkaline denaturation method (Chen, et al. DNA 4, 165–170 (1985); Haltiner et al., Nucleic Acids Research, 13, 1015–1026, (1985); and Hattori et al., Anal. Bio. Chem. 152, 232–238 (1986)).

The primed sequencing methods useful in the present invention are well known in the art. Any enzymatic priming method for determining DNA sequence is suitable in the random priming as well as in the directed priming methods of the present invention. These methods have in common the association of a primer with a complementary sequence on the nucleic acid molecule being sequenced. The preferred sequencing technique is that described originally by Sanger, Proc. Nat. Acad. Sci. U.S.A., 74, 5463–5467 (1977) and subsequently modified, in which DNA chain growth is terminated by means of 2', 3'-dideoxynucleoside triphosphates. The modifications for improving efficiency of such methods discussed in the background section of this specification may also be employed.

The primed nucleic acid molecule is incubated in the presence of a polymerizing enzyme. To do so, the nucleic acid molecule or the vector that contains the nucleic acid molecule is mixed with a primer or primer combination and with a polymerizing enzyme under conditions suitable for forming an oligonucleotide-primed substrate for nucleotide sequencing.

The polymerizing enzyme, the nucleic acid molecule and the primer are incubated under conditions suitable for primed synthesis of DNA that can be used for determining nucleotide sequence. Such conditions include the presence of additional materials such as, for example, buffers, magnesium and other ions, additional proteins and nucleoside triphosphates.

The polymerizing enzyme may, for example, be a polymerase or a reverse transcriptase. Some suitable polymerizing enzymes include, for example, Klenow fragment of E. coli DNA polymerase, T7 DNA polymerase, T7 DNA polymerase that has been modified to reduce its exonuclease activity, Taq DNA polymerase, AMV transcriptase and M-MuLV reverse transcriptase. T7 DNA polymerase that has been modified to reduce its exonuclease activity has been described by Tabor, et at., Proc. Nat. Acad. Sci. U.S.A., 84, 4767–4771 (1987) and is available from United States Biochemical Corporation, Cleveland, Ohio, as are detailed protocols for using it to determine nucleotide sequence.

The lengths of the resulting fragments may be resolved by methods that are known in the art. Such methods include, for example, gel electrophoresis.

The resolved fragments may be detected by methods that are known in the art. For example, the fragments may be labelled with a radioactive, fluorescent or chemically reactive atom or molecule and the labels detected.

The number of nucleotides sequenced following each replication is limited by the resolution of the particular technique used. Currently, approximately 500 nucleotides may be sequenced per replication reaction.

I claim:

1. A statistically-based random-priming method for determining nucleotide sequence in a nucleic acid template having a completely unknown or partly known nucleotide sequence by priming within a region of the template for which the nucleotide sequence is not known, the method comprising the steps of:
  a) supplying a template for which the approximate total length of unknown nucleotide sequence is known;
  b) selecting a primer or primer combination whose length or lengths relative to the template length are such that the probability P(1) of priming at a single site within the total length of unknown nucleotide sequence in the template is about 0.291–0.368, but excluding any primer that would prime in any part of the template where the nucleotide sequence is known;
  c) forming an incubation mixture comprising:
    i) the template;
    ii) the primer or primer combination selected in step b); and
    iii) a polymerizing enzyme;
  d) incubating the mixture of step c) under conditions appropriate for primed synthesis of DNA to generate products suitable for determining the nucleotide sequence in the template;
  e) analyzing the products of step d) to determine nucleotide sequence, which will be determinable only if priming occurred in step d) and was at a single site in the template; and
  f) if necessary, repeating steps b)–e), using different primers or primer combinations, until the nucleotide sequence has been determined.

2. The method of claim 1 wherein the primer combination is a two-primer combination.

3. The method of claim 1 wherein the primer combination is a three-primer combination.

4. The method of claim 1 wherein the primer or primer combination is selected from a primer library.

5. The method of claim 1 wherein the primer is an oligonucleotide 6, 7, 8, 9 or 10 bases long.

6. The method of claim 1 wherein the primer is selected from a primer library comprised of hexamers, heptamers, octamers, nonamers, decamers and primer combinations thereof.

7. The method of claim 1 wherein the nucleic acid template is DNA.

8. The method of claim 1 wherein the nucleic acid template is RNA.

9. A statistically-based directed-priming method that uses primers selected from a primer library to determine nucleotide sequence in a nucleic acid template having a nucleotide sequence which is partly known and partly unknown, the method comprising the steps of:
  a) supplying a template of known approximate length;
  b) supplying a primer library containing primers having lengths relative to the template length such that the probability P(O) that an individual primer will have no perfectly complementary priming site in any unknown nucleotide sequence in the template is greater than about 0.25, said library being of a size that the average priming interval is less than about half the average length of nucleotide sequence that can be determined from a single priming site;
  c) selecting from the primer library a primer that is perfectly complementary to one and only one site in the known nucleotide sequence in the template;
  d) forming an incubation mixture comprising:
    i) the template;
    ii) the primer selected in step c); and
    iii) a polymerizing enzyme;
  e) incubating the mixture of step d) under conditions appropriate for primed synthesis of DNA to generate products suitable for determining nucleotide sequence in the template; and
  f) analyzing the products of step e) to determine nucleotide sequence, which will be determinable only if the priming step e) was at a single site in the template.

10. The method of claim 9 wherein the primer library is comprised of hexamers, heptamers, octamers, nonamers, decamers and primer combinations thereof.

11. The method of claim 10 wherein the nucleic acid template is DNA.

12. The method of claim 10 wherein the nucleic acid template is RNA.

13. A statistically-based combined random- and directed-priming method for determining nucleotide sequence in a nucleic acid template having a completely unknown or partly known nucleotide sequence, comprising the steps of:
  a) supplying a template of known approximate length and for which the approximate total length of unknown nucleotide sequence is known;
  b) supplying a primer library containing primers having lengths relative to the template length such that the probability P(0) that an individual primer will have no perfectly complementary priming site in any unknown nucleotide sequence part in the template is greater than about 0.25, said library being of a size that the average priming interval is less than about half the average length of nucleotide sequence that can be determined from a single priming site;
  c) selecting from the primer library a primer or primer combination whose length or lengths are such that the probability P(1) of priming at a single site within the total length of the unknown nucleotide sequence part in the template is about 0.291–0.368, but excluding any primer that would prime in any part of the template for which the nucleotide sequence is known;
  d) forming an incubation mixture comprising:
    i) the template;
    ii) the primer or primer combination selected in step c); and
    iii) a polymerizing enzyme;
  e) incubating the mixture of step d) under conditions appropriate for primed synthesis of DNA to generate products suitable for determining nucleotide sequence in the template;
  f) analyzing the products of step e) to determine nucleotide sequence, which will be determinable only if priming occurred in step e) and was at a single site in the template;
  g) if necessary, repeating steps c)–f), using different primers or primer combinations, until nucleotide sequence information is determined;
  h) selecting from the primer library a primer that is perfectly complementary to one and only one site in the nucleotide sequence which is known in the template;
  i) forming an incubation mixture comprising:
    i) the template;
    ii) the primer selected in step h; and
    iii) a polymerizing enzyme;

j) incubating the mixture of step i) under conditions appropriate for primed synthesis of DNA to generate products suitable for determining nucleotide sequence in the template; and k) analyzing the products of step j) to determine nucleotide sequence, which will be determinable only if the priming in step j) was at a single site in the template.

14. The method of claim 13 wherein the primer combination selected in step c) is a two-primer combination.

15. The method of claim 13 wherein the primer combination selected in step c) is a three-primer combination.

16. The method of claim 13 wherein the primer library is comprised of hexamers, heptamers, octamers, nonamers, decamers and primer combinations thereof.

17. The method of claim 13 wherein the nucleic acid template is DNA.

18. The method of claim 13 wherein the nucleic acid template is RNA.

* * * * *